United States Patent [19]

Heelis et al.

[11] Patent Number: 5,000,193

[45] Date of Patent: Mar. 19, 1991

[54] MEDICAL SWAB DEVICE

[75] Inventors: Donald Heelis, Mississauga; Mark Semenuk, Downsview; Robert Zawydiwski, Stoney Creek, all of Canada

[73] Assignee: ADI Diagnostics Inc., Rexdale, Canada

[21] Appl. No.: 226,762

[22] Filed: Aug. 1, 1988

[51] Int. Cl.⁵ ............................................. A61B 10/00
[52] U.S. Cl. ........................................ 128/760; 604/1
[58] Field of Search ......................................: 604/1-3, 604/187, 231, 184, 222; 128/756, 760, 762, 765; 401/13; 15/260

[56] References Cited

U.S. PATENT DOCUMENTS

| | | | |
|---|---|---|---|
| 1,705,256 | 3/1929 | Krusi | 604/2 |
| 3,751,346 | 8/1973 | Elbreder | 15/260 |
| 4,014,322 | 3/1977 | Shah | 128/760 |
| 4,418,702 | 12/1983 | Brown et al. | 128/760 |
| 4,747,719 | 5/1988 | Parkin | 604/3 |

FOREIGN PATENT DOCUMENTS

| | | | |
|---|---|---|---|
| 2329443 | 6/1973 | Fed. Rep. of Germany | 128/756 |
| 0582420 | 12/1924 | France | 604/1 |

*Primary Examiner*—John D. Yasko
*Assistant Examiner*—A. Gutowski
*Attorney, Agent, or Firm*—Wyatt, Gerber, Burke & Badie

[57] ABSTRACT

A device is described for expressing liquid absorbed by the tip of a medical swab. The device comprises a barrel and a plunger slidable within the barrel for squeezing the tip of the swab. Liquid is discharged through a flow channel in the container or in the swab shaft. The device is useful particularly to recover small volumes of swab-absorbed liquid where necessary e.g. to carry out clinical essays.

15 Claims, 2 Drawing Sheets

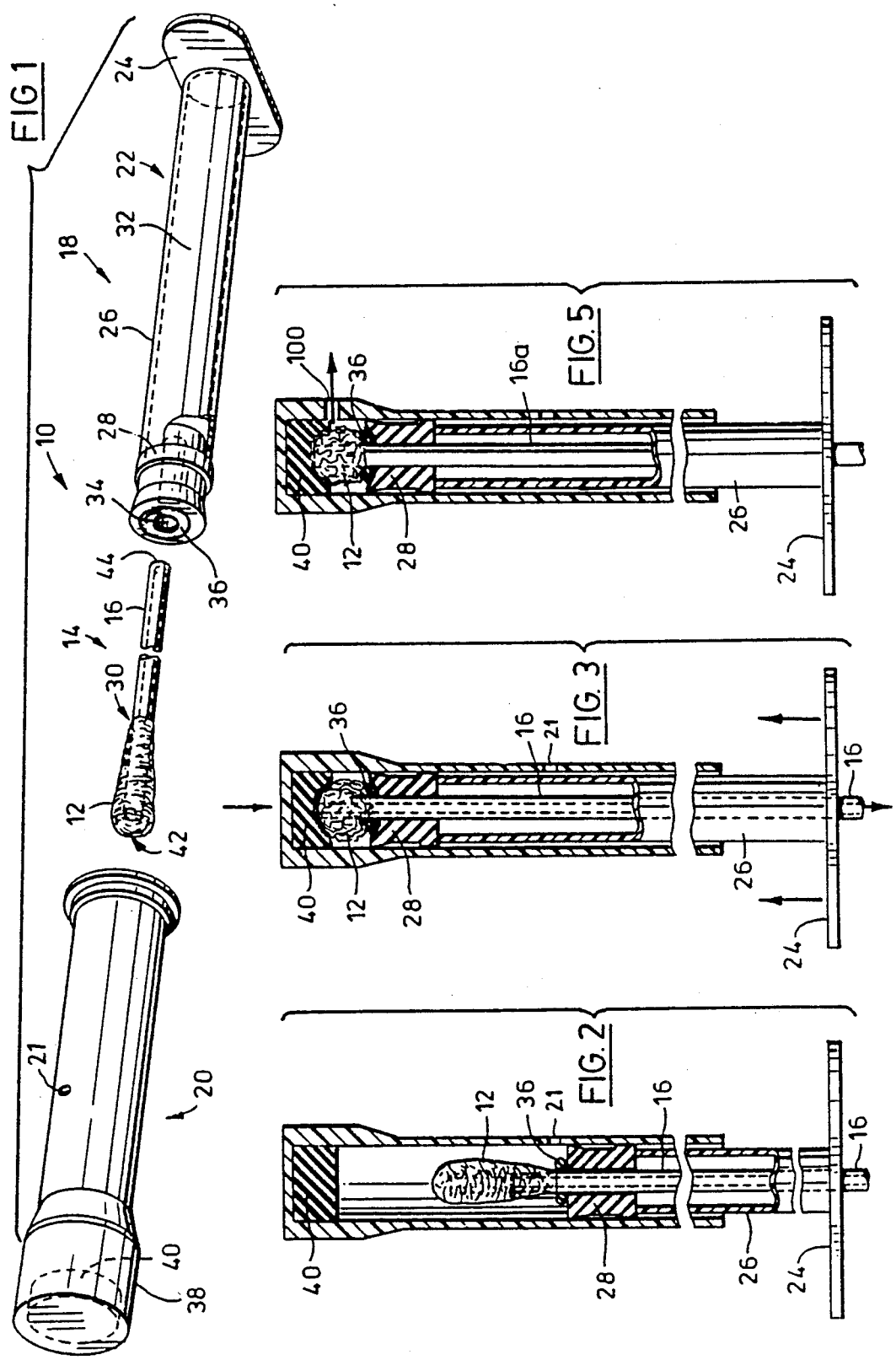

MEDICAL SWAB DEVICE

FIELD OF THE INVENTION

This invention relates generally to medical swabs of the type used primarily for collecting biological specimens for purposes of performing a variety of clinical tests on those specimens.

BACKGROUND TO THE INVENTION

Medical swabs in general are known in the art for use in collecting biological specimens from a patient. Such medical swabs commonly comprise an enlarged swab tip of absorbent material on one end of an elongated swab shaft used to direct the swab into contact with a chosen sampling site to collect a specimen on the swab tip. Typically, suspensions of the collected specimen are then prepared for subsequent analysis by immersing the specimen-coated swab tip directly into an appropriate liquid e.g. buffer or saline solution optionally containing an extraction agent such as detergent, nitrous acid, enzyme or the like, using a swirling action to release and disperse the specimen into the liquid.

When a small volume of suspension, such as a volume measurable in microlitres ($\mu l$) is prepared by swab immersion, it becomes critically important to express liquid efficiently from the absorbent swab tip before disposing of the swab, so that an adequate volume of the prepared suspension can be recovered for subsequent analysis.

Expression of liquid from the swab tip is routinely attempted by rolling and pressing the swab tip against an internal wall of the container in which the suspension has been prepared. However, the inefficiency with which liquid is expressed using this technique has prompted the use of mechanical aids that enhance expression of swab-absorbed liquid. One such mechanical aid is available as a component of a kit for diagnosing Strep throat infection sold under the name Test-Pack ™ by Abbott Laboratories. The mechanical aid is a conical tube of deformable plastic adapted to accommodate a swab tip and to contain liquid expressed therefrom. In use, the specimen-coated swab tip is placed into the tube with an extraction solution, the swab is twirled to release specimen and then the swab is withdrawn. As the swab is withdrawn, the tube is deformed by squeezing to engage the tip while the swab is rotated, in an effort to express liquid thoroughly from the swab into the tube. The efficiency with which liquid is removed from the swab when the tube is used is thus entirely dependent on the user's ability properly to coordinate the actions of squeezing and twirling. Further, the actions required to manipulate the swab and tube can be tiresome for clinicians or analysts who may perform dozens or even hundreds of such tests in a single day.

An object of the present invention is to provide a device which facilitates the expression of absorbed liquid from a swab tip in an efficient manner.

SUMMARY OF THE INVENTION

A device is provided for use with a medical swab to express liquid absorbed by the swab tip. The device of the invention is adapted to compress the swab tip between two opposed reaction members, at least one of the reaction members being displaceable 10 toward the other to effect the compression.

According to one aspect of the invention there is provided a device, for use in association with a medical swab having an elongated shaft and an absorbent tip at one end of the shaft, comprising opposed reaction elements, means for supporting said swab with its tip between said elements, means for guiding said elements in movement towards each other and a discharge channel having its inlet end communicating with a space between the reaction elements to allow liquid expressed from a swab tip to be discharged from the device. Preferably, the means for supporting said swab tip comprises an opening in one of said reaction elements through which the shaft of the swab is passed. Further, preferably, one of the reaction elements comprises a barrel and the other a plunger slidable within the barrel.

In one embodiment of this device the liquid discharge channel is formed in the barrel component of the device. Alternatively and in accordance with a preferred embodiment of the invention, the device is used in combination with a medical swab having a hollow shaft. In this embodiment, the hollow of the shaft serves as the discharge channel, extending from the absorbent tip to the end of the shaft and thus serving to direct flow of expressed liquid for discharge at a chosen site.

In general, the efficiency with which the present device expresses absorbed liquid from the tip of a swab is enhanced relative to methods known and currently used in the art. Moreover, because the tip is trapped in a contained environment harmful liquids can be recovered from the tip without significant health risks to the user of the device. As will be appreciated from the following detailed description of a preferred form of the invention, the device allows for efficient liquid expression using a one handed operation that simplifies the procedure for clinicians. Other features and advantages will also be apparent from the following detailed description taken in conjunction with the accompanying drawings which illustrate, by way of example, the principles of the invention.

BRIEF DESCRIPTION OF THE DRAWINGS

FIG. 1 is an exploded, perspective view of a liquid expressing device,

FIG. 2 is a sectional view of the assembled device positioned for expression of liquid from the tip of a swab, FIG. 3 is a sectional view of the device, showing positioning of the reaction members when the swab tip is compressed, FIG. 5 is a sectional view similar to FIG. 3 but showing an alternative embodiment having a flow channel through the container.

DETAILED DESCRIPTION OF THE PREFERRED EMBODIMENTS

Figure 4:
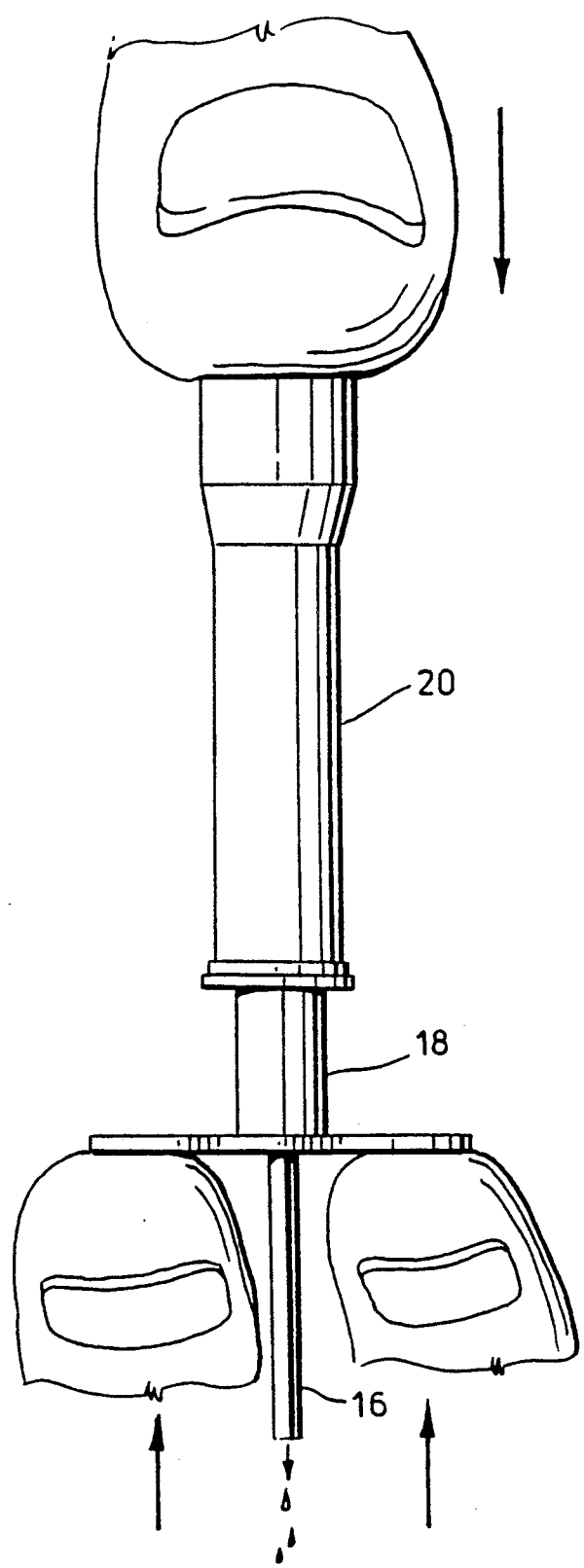
FIG. 4 is a perspective view showing the device in use.

The device, referred to generally in FIG. 1 by the reference show numeral 10, is provided for use in expressing liquid from the tip 12 of a medical swab 14 having a hollow, elongated shaft 16 (for compactness shown broken away). The device 10 comprises a plunger assembly 18 and a barrel assembly 20.

Plunger assembly 18 is adapted for slidable engagement on the swab shaft 16 and comprises a plunger 22 having a handle 24 and a stem 26 both of which are formed, preferably as an integral unit, from a plastic material that is sufficiently rigid to transmit a compressing force applied by the user. Plastics such as polystyrene or high density polyethylene or polypropylene are suitable for this purpose. First reaction member 28 is mounted on the forward end of stem 26 for engagement with the proximal end 30 of the swab tip 12 during use of the device. The reaction member 28 is formed of a resiliently deformable plastic such as thermoplastic rubber which allows that member to conform to the shape of the swab tip upon engagement therewith.

Plunger assembly 18 is provided with a central passage 32 extending therethrough for receiving the swab shaft in a slidably engaging manner. While the passage 32 may have a bore of uniform diameter along its length, it is sufficient, for the purpose of guiding reaction member 28 into contact with the swab tip that the aperture 34 defined by the reaction member has a diameter frictionally and slidingly to engage the shaft. To facilitate the guiding function of aperture 34 and to prevent flow of expressed liquid from the swab tip into the central passage during use, an O-ring 36 is provided.

Barrel assembly 20 is a tubular rigid plastic barrel 38 having a bore sized for frictional and sliding engagement of reaction member 28. Second reaction member 40 is disposed in the bottom of container 38 for abutment with the distal end 42 of the swab tip.

To use the device 10, plunger assembly 18 is mounted on the hollow swab shaft 16, by inserting the free end 44 of the shaft into aperture 32 and then sliding the shaft further into assembly 18 until the assembly fully engages the shaft. The assembly 18 may be mounted on the shaft after the sample is collected on the swab tip or after a liquid suspension of the sample is prepared, if desired. It i s preferable, however, to mount the assembly on the shaft before using the swab to collect a specimen to minimize subsequent user contact with the specimen. In this regard, the plunger assembly 18 is useful as a handle for manipulating the swab during sample collection. It will be appreciated that the assembly and swab shaft should be slidably but frictionally engaged to the extent that the mild force applied on the assembly during sampling is insufficient to move the assembly down the shaft.

Once the sample is collected and the assembly 18 is engaged on the shaft, the swab tip is typically immersed in a liquid to prepare a suspension of the sample for analysis. To express liquid absorbed by the swab tip during its immersion the assembly 18 is first pushed down the shaft to a resting position just above the proximal end of the swab tip, as shown in FIG. 2.

Assembly 18 is then inserted into the barrel 38 of assembly 20 to trap the swab tip between reaction members 28 and 40. To express liquid from the tip, plunger 22 is actuated manually, as shown in FIG. 4, causing the tip to be compressed between members 28 and 40 in the manner shown in FIG. 3. It will be appreciated that the air in front of the plunger will be compressed and tend to force liquid through the hollow shaft of the swab. To prevent this from happening until the swab and plunger are fully located within the barrel a vent 21 is formed in the barrel. That vent is, of course, isolated from the swab containing portion of the barrel as the plunger is advanced into the barrel. As will be seen in FIG. 3, the swab tip becomes compacted between the reaction members which deform somewhat about the tip to accent the compressing action applied by the user. In this way, the reaction members co-act within the container to express liquid from the tip.

In the embodiment of the device depicted in FIGS. 1-4, a swab useful in combination therewith comprises a hollow shaft. The hollow of the shaft allows for flow communication between the tip and the free end 44 of the shaft, and thus serves as a channel for the discharge of liquid expressed from the swab tip when the device is used. In this connection, the shaft of the swab facilitates delivery of expressed liquid to a selected, specific location by guiding the liquid therethrough. Moreover, the mat of fibres forming the tip of the swab serves as a filter for preventing large and undesired particles collected during sampling or specimen extraction from flowing through the hollow shaft. For these reasons, it is preferable to employ a swab having a hollow shaft when using the device described above.

An alternative embodiment of the invention is depicted in FIG. 5. This embodiment of the device is adapted particularly for use in combination with a swab 16a having a solid shaft. The device per se is substantially the same in dimension and design as the embodiment illustrated in FIGS. 1-4 but provides a discharge channel 100 in the sidewall of the container. Since the discharge channel also serves as a vent no separate vent such as vent 21 in FIGS. 1 through 4 is necessary. The channel 100 communicates with the swab tip during compression to achieve the same effect as described above to allow expressed liquid to be discharged from the device and may be provided with a tubular extension (not shown) for guiding the flow of discharged liquid to a selected site.

The device of the invention may be sold per se in a package comprising its two assembly components together with an instructional pamphlet describing its use. Alternatively and preferably, the device of the invention is sold as described above in combination with a swab having a shaft girth and tip sized for accommodation by the device. When sold in combination with a swab having a hollow shaft, the device of the invention will be of the form described with reference to FIG. 1-4, since a channel for discharge of expressed liquid is provided inherently by the shaft of such a swab. When sold in combination with a swab having a solid shaft, the device will be of a form such as that depicted in FIG. 5 which is provided with a discharge channel in the barrel. Further, it may be desirable to provide the device and swab in a pre-assembled form in which the plunging assembly is mounted on the shaft of the swab to reduce the risk of user contact with the collected specimen. Since the device will be useful as a tool for microbiologists and clinicians in manipulating microbial and other such samples, it is clearly desirable to package the components aseptically although the device of the invention may be autoclaved on site to ensure sterility.

We claim:

1. For use in association with a medical swab having an elongated shaft and an absorbent tip at one of the shaft, a device useful in recovering liquid abosebed by the tip, comprising:

a plunger member movable within a barrel member between operative and inoperative conditions;

a pair of opposed reaction elements disposed within said barrel member, at least one of said reaction elements being moveable therein towards the other of said reaction elements upon movement of said plunger member to said operative condition, one of said plunger member and said one reaction element being in sealing engagement with said barrel member;

means for supporting a swab with its tip between said reaction elements, wherein said means for supporting said swab tip comprises an opening in one of said reaction elements through which the shaft of the swab is passed, and a discharge channel having an inlet end communicating with a space between said reaction elements to allow liquid expressed from a swab tip to be discharged from said device.

2. The device according to claim 1 wherein at least one of said one reaction element and said other reaction element are formed of resilient, deformable plastic material to conform to a swab tip when the tip is compressed therebetween.

3. For use in association with a medical swab having an elongated shaft and an absorbent tip at one end of the shaft, a device useful in recovering liquid absorbed by the tip comprising:

a plunger member moveable within a barrel member between operative and inoperative conditions;

a pair of opposed reaction elements disposed within said barrel member, at least one of said reaction elements being moveable therein towards the other of said reaction elements upon movement of said plunger member to said operative condition, one of said plunger member and said one reaction element being in sealing engagement with said barrel member, said plunger member having a distal end and said barrel member including a base having a bottom surface, said distal end constituting said one reaction element and said bottom surface constituting the other reaction element;

means for supporting a swab with its tip between reaction elements; and a discharge channel having an inlet end communicating with a space between said reaction elements to allow liquid expressed from a swab tip to be discharged from said device, said discharge channel being defined by a through passage provided in said plunger member or in the base of said barrel member with the walls of said through passage constituting said means for supporting a swab tip.

4. A device according to claim 3 wherein said through passage is provided in said plunger member and is dimensioned to engage frictionally with the shaft of a swab.

5. A device according to claim 4 further comprising a sealing member provided on said plunger member adjacent said distal end, said sealing member engaging with the shaft of a swab to prevent passage of liquid expressed from a swab tip between the walls of said through passage and a swab shaft positioned in said through passage.

6. For use in association with a medical swab having an elongated shaft and an absorbent tip at one end of the shaft, a device useful in recovering liquid absorbed by the tip comprising:

a plunger member moveable within a barrel member between operative and inoperative conditions, said plunger member has a distal end and said barrel member includes a base having a bottom surface, said distal end constituting said one reaction element and said bottom surface constituting the other reaction element, and wherein at least one of said distal ends and said bottom surface are formed of resilient, deformable plastic material to conform to a swab tip when the tip is compressed therebetween, a pair of opposed reaction elements disposed within said barrel member, at least one of said reaction elements being moveable therein towards the other of said reaction elements upon movement of said plunger member to said operative condition, one of said plunger member and said one reaction element being in sealing engagement with said barrel member;

means for supporting a swab with its tip between said reaction elements; and a discharge channel having an inlet end communicating with a space between said reaction elements to allow liquid expressed from a swab tip to be discharged from said device.

7. In combination, a medical swab having an absorbent tip on one end of an elongated shaft and a device useful in recovering liquid absorbed by the tip, comprising:

a plunger member movable within a barrel member between operative and inoperative conditions;

a pair of opposed reaction elements disposed within said barrel member, at least one of said reaction elements being moveable therein towards the other of said reaction elements upon movement of said plunger member to said operative condition, one of said plunger member and said one reaction element being in sealing engagement with said barrel member;

means for supporting said swab with its tip between said reaction elements; and a discharge channel having an inlet end communicating with a space between said reaction elements to allow liquid expressed from said swab tip to be discharged from said device.

8. The combination of claim 7 wherein said plunger member has a distal end and said barrel member includes a base having a bottom surface, said distal end constituting said one reaction element and said bottom surface constituting the other reaction element.

9. The combination of claim 8 wherein at least one of said distal end and said bottom surface are formed of resilient, deformable plastic material to conform to said swab tip when the tip is compressed therebetween.

10. The combination of claim 7 wherein said means for supporting said swab tip comprises an opening in one of said reaction elements through which the shaft of the swab is passed.

11. The combination of claim 8 wherein said discharge channel is defined by a through passage provided in said plunger member or in the base of said barrel member.

12. The combination of claim 11 wherein walls of said through passage constitute means for supporting said swab.

13. The combination of claim 12 wherein said medical swab has a hollow shaft and wherein said through passage is dimensioned to engage frictionally with said shaft and wherein liquid expressed from said swab tip passes through the discharge channel defined by said hollow shaft.

14. The combination of claim 10 wherein at least one of said one reaction element and said other reaction element are formed of resilient, deformable plastic material to conform to said swab tip when the tip is compressed therebetween.

15. The combination of claim 13 further comprising a sealing member provided on said plunger member adjacent said distal end, said sealing member engaging with the shaft of said swab to prevent the passage of liquid expressed from said swab tip between the walls of said through passage and the swab shaft.

* * * * *